United States Patent
Fischer et al.

(10) Patent No.: US 7,329,634 B2
(45) Date of Patent: Feb. 12, 2008

(54) 3-PHENYL SUBSTITUTED 3-SUBSTITUTED-4KETOLACTAMS AND KETOLACTONES

(75) Inventors: Reiner Fischer, Monheim (DE); Stefan Lehr, Liederbach (DE); Thomas Bretschneider, Lohmar (DE); Mark Wilhelm Drewes, Langenfeld (DE); Dieter Feucht, Eschborn (DE); Jörg Konze, Köln (DE); Olga Malsam, Rösrath (DE); Karl-Heinz Kuck, Langenfeld (DE); Guido Bojack, Wiesbaden (DE); Thomas Auler, Leichlingen (DE); Martin Hills, Idstein (DE); Heinz Kehne, Hofheim (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/542,561

(22) PCT Filed: Jan. 7, 2004

(86) PCT No.: PCT/EP2004/000037

§ 371 (c)(1),
(2), (4) Date: Dec. 15, 2005

(87) PCT Pub. No.: WO2004/069841

PCT Pub. Date: Aug. 19, 2004

(65) Prior Publication Data

US 2006/0094773 A1 May 4, 2006

(30) Foreign Application Priority Data

Jan. 20, 2003 (DE) ................................ 103 01 805

(51) Int. Cl.
| | |
|---|---|
| *A01N 43/36* | (2006.01) |
| *A01N 43/08* | (2006.01) |
| *A61K 31/40* | (2006.01) |
| *A61K 31/335* | (2006.01) |
| *C07D 207/00* | (2006.01) |
| *C07D 321/00* | (2006.01) |
| *C07D 493/00* | (2006.01) |
| *C07D 209/54* | (2006.01) |
| *C07D 209/96* | (2006.01) |
| *C07D 307/00* | (2006.01) |

(52) U.S. Cl. .................. 504/283; 504/294; 514/425; 514/449; 548/400; 548/407; 548/577; 549/200; 549/330; 549/429

(58) Field of Classification Search ............... 504/283, 504/294; 514/425, 449; 549/200, 330, 429; 548/400, 407, 577
See application file for complete search history.

(56) References Cited

U.S. PATENT DOCUMENTS

| | | | |
|---|---|---|---|
| 5,622,917 A | 4/1997 | Fischer et al. | 504/283 |
| 5,847,211 A | 12/1998 | Fischer et al. | 564/123 |
| 5,994,274 A | 11/1999 | Fischer et al. | 504/282 |
| 6,316,486 B1 | 11/2001 | Lieb et al. | 514/411 |
| 6,380,246 B1 | 4/2002 | Lieb et al. | 514/462 |
| 6,759,548 B2 | 7/2004 | Fischer et al. | 560/81 |
| 6,858,741 B2 | 2/2005 | Lieb et al. | 549/67 |
| 2002/0022575 A1 | 2/2002 | Fischer et al. | 504/221 |
| 2003/0144504 A1 | 7/2003 | Fischer et al. | 544/54 |
| 2003/0199572 A1 | 10/2003 | Lieb et al. | 514/451 |

FOREIGN PATENT DOCUMENTS

| | | | |
|---|---|---|---|
| JP | 2000086628 | * | 3/2000 |
| WO | 98/25928 | | 6/1998 |
| WO | 03/029213 | | 4/2003 |
| WO | 03/045957 | | 6/2003 |

OTHER PUBLICATIONS

Chem. Ind., 37, (month unavailable) 1985, pp. 730-732, Harry R. Ungerer, "Schiffsfarben—eine Spezialität der seenahen Lackindustrie".
Patent Abstracts of Japan vol. 1998, No. 14, Dec. 31, 1998 & JP 10 258555 A (Citizen Watch Co Ltd), Sep. 29, 1998.

* cited by examiner

*Primary Examiner*—Alton Pryor
(74) *Attorney, Agent, or Firm*—Richard E. L. Henderson

(57) ABSTRACT

The invention relates to novel 3-phenyl-substituted, 3-substituted 4-ketolactams and -lactones of the formula (I)

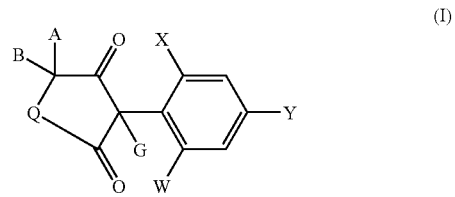

in which Q, W, X, Y, A, B and G are as defined in the disclosure, to processes and intermediates for their preparation and to their use as pesticides and herbicides.

9 Claims, No Drawings

3-PHENYL SUBSTITUTED 3-SUBSTITUTED-4KETOLACTAMS AND KETOLACTONES

The present patent application has been filed under 35 U.S.C. 371 as a national stage application of PCT/EP2004/000037, filed Jan. 7, 2004, which was published in German as International Patent Publication WO 2004/069841 on Aug. 19, 2004, and is entitled to the right of priority of German Patent Application 1-03 01 805.0, filed Jan. 20, 2003.

The invention relates to novel 3-phenyl-substituted, 3-substituted 4-ketolactams and -lactones, to processes and intermediates for their preparation and to their use as pesticides and herbicides.

It is already known that certain phenyl-substituted 3-halo-4-ketolactams (JP-A-10-258 555) and phenyl-substituted 3-halo-4-ketolactones (JP-A-10-258 555) act as acaricides or insecticides and/or herbicides.

However, in particular at low application rates and concentrations, the activity and activity spectrum of these compounds is not always entirely satisfactory. Furthermore, the compatibility of these compounds with the crop plants is not always sufficient.

This invention now provides novel compounds of the formula (I)

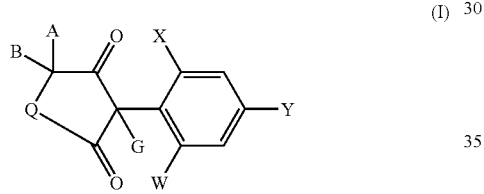

(I)

in which

Q represents oxygen or N—H,

W represents alkyl,

X represents hydrogen, halogen or alkyl,

Y represents halogen or alkyl, with the proviso that at least one of the radicals X or Y represents halogen, A represents haloalkyl, alkyl, alkoxyalkyl, benzyl or optionally substituted cycloalkyl, B represents hydrogen or alkyl, A and B together with the carbon atom to which they are attached represent a saturated, optionally alkyl- or haloalkyl-substituted cycle, G represents halogen or nitro.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, their preparation and use and compositions comprising them. However, hereinbelow, for the sake of simplicity, compounds of the formula (I) are always referred to, although this is meant to include both the pure compounds and, if appropriate, mixtures having varying proportions of isomeric compounds.

Including the meanings of Q, the following principal structures (I-1) to (I-2),

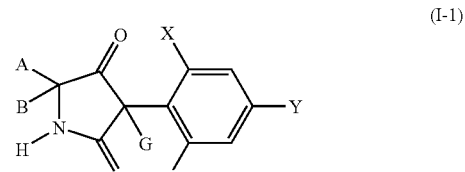

(I-1)

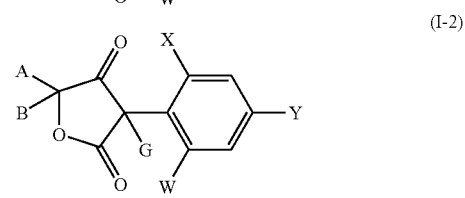

(I-2)

result, in which

A, B, G, W, X and Y are as defined above.

A) Furthermore, it has been found that compounds of the formulae (I-1) to (I-2)

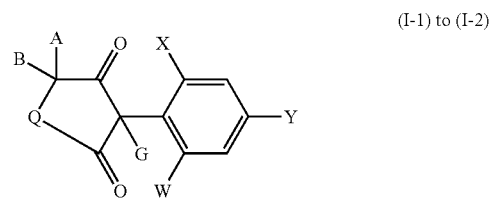

(I-1) to (I-2)

in which A, B, Q, W, X and Y are as defined above and G represents halogen, preferably chlorine and bromine, are obtained when compounds of the formulae (II-1) to (II-2)

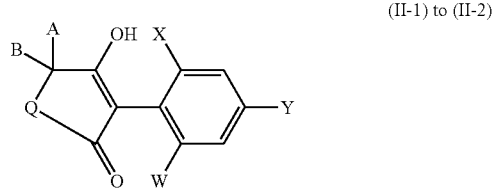

(II-1) to (II-2)

in which A, B, Q, W, X and Y are as defined above
are reacted with halogenating agents in the presence of a solvent and, if appropriate, in the presence of a free-radical initiator.

B) Furthermore, compounds of the formulae (I-1) to (I-2)

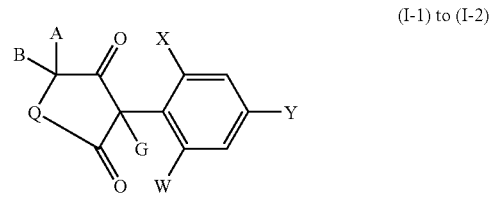

(I-1) to (I-2)

in which A, B, Q, W, X and Y are as defined above and G represents nitro, are obtained when compounds of the formulae (II-1) to (II-2)

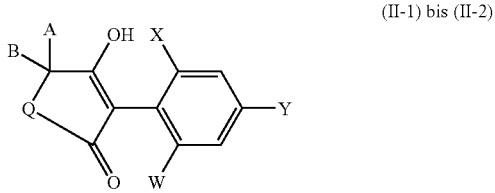

(II-1) bis (II-2)

in which

A, B, Q, W, X and Y are as defined above are reacted with nitrating agents, such as, for example, fuming nitric acid, in the presence of a solvent.

Some of the compounds of the formulae (II-1) to (II-2)

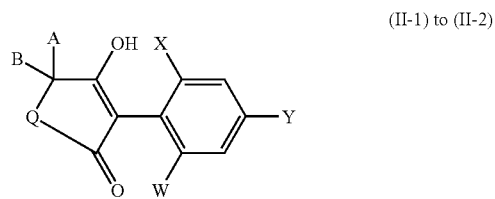

(II-1) to (II-2)

in which

A, B, Q, W, X and Y are as defined above, which compounds are required for processes A and B, are known compounds (for example from EP-A 668 267, WO 96/35 664, WO 97/02 243), or they can be synthesized by the processes described therein.

Suitable halogenating agents for process A are, for example, sulphuryl chloride, sulphuryl bromide, thionyl chloride, thionyl bromide, imides, such as, for example, N-bromosuccinimide or N-chlorosuccinimide chlorosulphonic acid, and also hypochlorites, such as, for example, tert-butyl hypochlorite.

Suitable nitrating agents for process B are fuming nitric acid, and also "nitrating acid mixtures".

Furthermore, it has been found that the novel compounds of the formula (I) have very good activity as pesticides, preferably as insecticides and/or acaricides and/or herbicides.

The formula (I) provides a general definition of the compounds according to the invention. Preferred substituents or ranges of the radicals listed in the formulae mentioned above and below are illustrated below:

Q preferably represents oxygen or N—H,
W preferably represents $C_1$-$C_4$-alkyl,
X preferably represents hydrogen, halogen or $C_1$-$C_4$-alkyl,
Y preferably represents halogen or $C_1$-$C_2$-alkyl,
  with the proviso that at least one of the radicals X or Y represents halogen,
A preferably represents $C_1$-$C_8$-alkyl, $C_1$-$C_4$-haloalkyl, $C_1$-$C_4$-alkoxy-$C_1$-$C_2$-alkyl, benzyl or represents $C_3$-$C_6$-cycloalkyl which is optionally mono- or disubstituted by $C_1$-$C_4$-alkyl, $C_1$-$C_4$-alkoxy or halogen,
B preferably represents hydrogen or $C_1$-$C_4$-alkyl,
A, B and the carbon atom to which they are attached preferably represent saturated $C_3$-$C_8$-cycloalkyl which is optionally mono- or disubstituted by $C_1$-$C_4$-alkyl or $C_1$-$C_2$-haloalkyl,
G preferably represents chlorine, bromine or nitro.

In the radical definitions mentioned as being preferred, halogen represents fluorine, chlorine, bromine and iodine, in particular fluorine, chlorine and bromine.

Q particularly preferably represents oxygen or N—H,
W particularly preferably represents methyl, ethyl or n-propyl,
X particularly preferably represents hydrogen, chlorine, bromine, methyl, ethyl or n-propyl,
Y particularly preferably represents chlorine, bromine, methyl or ethyl,
  with the proviso that at least one of the radicals X or Y represent halogen,
A particularly preferably represents $C_1$-$C_6$-alkyl, trifluoromethyl, $C_1$-$C_2$-alkoxy-$C_1$-$C_2$-alkyl, benzyl, or represents $C_3$-$C_6$-cycloalkyl which is optionally monosubstituted by $C_1$-$C_2$-alkyl, $C_1$-$C_2$-alkoxy, fluorine or chlorine,
B particularly preferably represents hydrogen or $C_1$-$C_2$-alkyl,
A, B and the carbon atom to which they are attached particularly preferably represent saturated $C_5$-$C_6$-cycloalkyl which is optionally monosubstituted by $C_1$-$C_2$-alkyl or trifluoromethyl,
G particularly preferably represents chlorine, bromine or nitro.

Q very particularly preferably represents oxygen or N—H,
W very particularly preferably represents methyl, ethyl or n-propyl,
X very particularly preferably represents hydrogen, chlorine, bromine, methyl or ethyl,
Y very particularly preferably represents chlorine, bromine, methyl or ethyl, with the proviso that at least one of the radicals X or Y represents halogen,
A very particularly preferably represents methyl, ethyl, n-propyl, isopropyl, n-butyl, sec-butyl, isobutyl, tert-butyl, trifluoromethyl, benzyl, cyclopropyl, cyclopentyl or cyclohexyl,
B very particularly preferably represents hydrogen, methyl or ethyl,
A, B and the carbon atom to which they are attached very particularly preferably represent saturated $C_6$-cycloalkyl which is optionally monosubstituted by methyl,
G very particularly preferably-represents chlorine or nitro.

Q especially preferably represents NH,
W especially preferably represents ethyl or n-propyl,
X especially preferably represents methyl, ethyl, chlorine or bromine,
Y especially preferably represents chlorine, bromine, methyl or ethyl, with the proviso that at least one of the radicals X or Y represents halogen,
A especially preferably represents methyl, ethyl, n-propyl, isopropyl, isobutyl, cyclopropyl or benzyl,
B especially preferably represents hydrogen, methyl or ethyl,
A, B and the carbon atom to which they are attached especially preferably represent saturated $C_6$-cycloalkyl, which is optionally substituted by methyl,
G especially preferably represents chlorine.

Q also especially preferably represents NH,
W also especially preferably represents methyl or ethyl,
X also especially preferably represents hydrogen,
Y also especially preferably represents chlorine or bromine,
A also especially preferably represents methyl,
B also especially preferably represents methyl, A, B and the carbon atom to which they are attached also especially preferably represent saturated $C_6$-cycloalkyl which is optionally monosubstituted by methyl, G also especially preferably represents chlorine.

Q moreover especially preferably represents oxygen,

W moreover especially preferably represents methyl or ethyl,

X moreover especially preferably represents methyl, chlorine or bromine,

Y moreover especially preferably represents methyl, bromine or chlorine, with the proviso that at least one of the radicals X or Y represents halogen, A, B and the carbon atom to which they are attached moreover especially preferably represents saturated $C_6$-cycloalkyl which is optionally monosubstituted by methyl, G moreover especially preferably represents chlorine.

The general or preferred radical definitions or illustrations listed above can be combined with one another as desired, i.e. including combinations between the respective ranges and preferred ranges. The definitions apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Saturated or unsaturated hydrocarbon radicals, such as alkyl or alkenyl, can in each case be straight-chain or branched as far as this is possible, including in combination with heteroatoms, such as, for example, an alkoxy.

Unless indicated otherwise, optionally substituted radicals can be mono- or polysubstituted where, in the case of polysubstitution, the substituents can be identical or different.

In addition to the compounds mentioned in the Preparation Examples, the following compounds of the formula (I-1) may be specifically mentioned:

TABLE 1

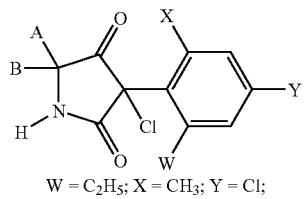

$W = C_2H_5; X = CH_3; Y = Cl;$

| A | B |
|---|---|
| $CH_3$ | $CH_3$ |
| $C_2H_5$ | $CH_3$ |
| $C_3H_7$ | $CH_3$ |

TABLE 1-continued

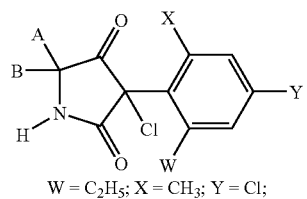

$W = C_2H_5; X = CH_3; Y = Cl;$

| A | B |
|---|---|
| $i$-$C_3H_7$ | $CH_3$ |
| $C_4H_9$ | $CH_3$ |
| $i$-$C_4H_9$ | $CH_3$ |
| $s$-$C_4H_9$ | $CH_3$ |
| $t$-$C_4H_9$ | $CH_3$ |
|  | $CH_3$ |
| 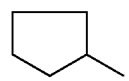 | $CH_3$ |
| 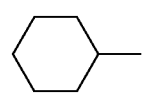 | $CH_3$ |
| —$(CH_2)_4$— | |
| —$(CH_2)_5$— | |
| —$CH_2$—$CHCH_3$—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$C(CH_3)_2$-$(CH_2)_2$- | |
| —$CH_2$—$(CHCH_3)_2$—$(CH_2)_2$— | |

TABLE 2

A and B are as stated in Table 1
$W = C_2H_5; X = C_2H_5; Y = Cl.$

TABLE 3

A and B are as stated in Table 1
$W = C_2H_5; X = CH_3; Y = Br.$

TABLE 4

A and B are as stated in Table 1
$W = C_2H_5; X = C_2H_5; Y = Br.$

TABLE 5

A and B are as stated in Table 1
$W = C_2H_5; X = Br; Y = C_2H_5.$

TABLE 6

A and B are as stated in Table 1
$W = C_2H_5; X = Cl; Y = Cl.$

TABLE 7

A and B are as stated in Table 1
W = C$_2$H$_5$; X = Cl; Y = Br.

TABLE 8

A and B are as stated in Table 1
W = C$_2$H$_5$; X = Br; Y = Cl.

TABLE 9

A and B are as stated in Table 1
W = C$_2$H$_5$; X = Br; Y = Br.

TABLE 10

A and B are as stated in Table 1
W = C$_2$H$_5$; X = Cl; Y = CH$_3$.

TABLE 11

A and B are as stated in Table 1
W = C$_2$H$_5$; X = Br; Y = CH$_3$.

TABLE 12

A and B are as stated in Table 1
W = C$_2$H$_5$; X = H; Y = Cl.

TABLE 13

A and B are as stated in Table 1
W = C$_2$H$_5$; X = H; Y = Br.

TABLE 14

A and B are as stated in Table 1
W = CH$_3$; X = CH$_3$; Y = Cl.

TABLE 15

A and B are as stated in Table 1
W = CH$_3$; X = CH$_3$; Y = Br.

TABLE 16

A and B are as stated in Table 1
W = CH$_3$; X = Cl; Y = CH$_3$.

TABLE 17

A and B are as stated in Table 1
W = CH$_3$; X = Br; Y = CH$_3$.

TABLE 18

A and B are as stated in Table 1
W = CH$_3$; X = Cl; Y = Cl.

TABLE 19

A and B are as stated in Table 1
W = CH$_3$; X = Cl; Y = Br.

TABLE 20

A and B are as stated in Table 1
W = CH$_3$; X = Br; Y = Cl.

TABLE 21

A and B are as stated in Table 1
W = CH$_3$; X = Br; Y = Br.

TABLE 22

A and B are as stated in Table 1
W = CH$_3$; X = H; Y = Cl.

TABLE 23

A and B are as stated in Table 1
W = CH$_3$; X = H; Y = Br.

TABLE 24

A and B are as stated in Table 1
W = C$_3$H$_7$; X = Br; Y = Br.

Using, for example, according to process (A), 3-[(2-ethyl-4-bromo-6-methyl)phenyl]-5,5-pentamethylenepyrrolidine-2,4-dione as starting material, the course of the process according to the invention can be represented by the following reaction scheme:

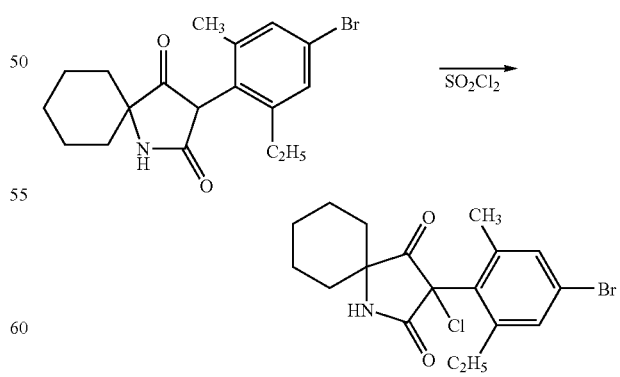

Using, for example, according to process (B), 3-[(2,4-dichloro-6-ethyl)phenyl]-5,5-dimethylpyrrolidine-2,4-dione, the course of the process according to the invention can be represented by the following reaction scheme:

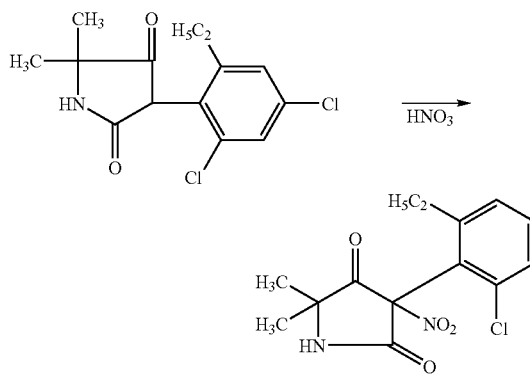

The process (A) is characterized in that compounds of the formula (II) in which A, B, Q, W, X and Y are as defined above are reacted in the presence of a diluent and a halogenating agent and, if appropriate, a free-radical initiator. Suitable free-radical initiators are, for example, benzoyl peroxide or azobisisobutyronitrile.

Suitable diluents for use in the process (A) according to the invention are all inert organic solvents. Preference is given to using hydrocarbons, such as benzene, toluene and xylene, furthermore ethers, such as dibutyl ether, tetrahydrofuran, dioxane, glycol dimethyl ether and diglycol dimethyl ether, moreover halogenated hydrocarbons, such as dichloromethane, chloroform, carbon tetrachloride, dichloroethane, chlorobenzene, dichlorobenzene, and also esters, such as ethyl acetate.

Suitable halogenating agents for process (A) are, for example, sulphuryl chloride, sulphuryl bromide, thionyl chloride, thionyl bromide, imides, such as, for example, N-bromosuccinimide and N-chlorosuccinimide, furthermore chlorosulphonic acid, and also hypochlorites, such as, for example, tert-butyl hypochlorite.

When carrying out the process (A) according to the invention, the reaction temperatures can be varied within a relatively wide range. In general, the process is carried out at temperatures between −40° C. and 150° C., preferably between 0° C. and 100° C.

The process (A) according to the invention is generally carried out under atmospheric pressure.

When carrying out the process (A) according to the invention, the reaction components of the formula (II) and the halogenating agents are generally employed in approximately equimolar amounts. However, it is also possible to use a relatively large excess (up to 3 mol) of one component or the other.

The process (B) is characterized in that compounds of the formula (II) in which A, B, Q, W, X and Y are as defined above is reacted in the presence of a diluent and in the presence of a nitrating agent.

Suitable diluents for use in the process (B) according to the invention are all inert organic solvents. Preference is given to using halogenated hydrocarbons, such as methylene chloride, chloroform, dichlorobenzene and dichloroethane.

Suitable nitrating agents are "nitrating acids", preferably fuming nitric acid.

When carrying out the process (B) according to the invention, the reaction temperatures can be varied within a relatively wide range. In general, the process is carried out at temperatures between −50° C. and 150° C., preferably between 0° C. and 80° C.

The process (B) according to the invention is generally carried out under atmospheric pressure.

When carrying out the process (B) according to the invention, the reaction components of the formula (II) and the nitrating agent are generally employed in approximately equimolar amounts. However, it is also possible to use a relatively large excess (up to 5 mol) of one component or the other.

The active compounds are suitable for controlling animal pests, in particular insects, arachnids and nematodes, which are encountered in agriculture, in forests, in the protection of stored products and of materials, and in the hygiene sector, and have good plant tolerance and favourable toxicity to warm-blooded animals. They may preferably be employed as crop protection agents. They are active against normally sensitive and resistant species and against all or some stages of development. The abovementioned pests include:

From the order of the Isopoda, for example,*Oniscus asellus, Armadillidium vulgare* and *Porcellio scaber.*

From the order of the Diplopoda, for example,*Blaniulus guttulatus.*

From the order of the Chilopoda, for example,*Geophilus carpophagus* and *Scutigera* spp.

From the order of the Symphyla, for example,*Scutigerella immaculata.*

From the order of the Thysanura, for example,*Lepisma saccharina.*

From the order of the Collembola, for example,*Onychiurus armatus.*

From the order of the Orthoptera, for example,*Acheta domesticus, Gryllotalpa* spp., *Locusta migratoria migratorioides,Melanoplus* spp. and *Schistocerca gregaria.*

From the order of the Blattaria, for example,*Blatta orientalis, Periplaneta americana, Leucophaea maderae, Blattella germanica.*

From the order of the Dermaptera, for example,*Forficula auricularia.*

From the order of the Isoptera, for example,*Reticulitermes* spp.

From the order of the Phthiraptera, for example,*Pediculus humanus* corporis, *Haematopinus* spp.,*Linognathus* spp., *Trichodectes* spp. and *Damalinia* spp.

From the order of the Thysanoptera, for example,*Hercinothrips femoralis, Thrips tabaci, Thrips palmi* and *Frankliniella accidentalis.*

From the order of the Heteroptera, for example,*Eurygaster* spp.,*Dysdercus intermedius, Piesma quadrata, Cimex lectularius, Rhodnius prolixus* and *Triatoma* spp.

From the order of the Homoptera, for example,*Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp.,*Macrosiphum avenae, Myzus* spp.,*Phorodon humuli, Rhopalosiphum padi, Empoasca* spp.,*Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example,*Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp.,*Euxoa* spp.,*Feltia* spp., *Earias insulana, Heliothis* spp.,*Mamestra brassicae, Panolis flammea, Spodoptera* spp.,*Trichoplusia ni, Carpocapsa pomonella, Pieris* spp.,*Chilo* spp.,*Pyrausta nubilalis, Ephe-* stia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus spp.,Oulema oryzae.

From the order of the Coleoptera, for example,*Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp.,*Oryzaephilus surinamensis, Anthonomus* spp.,*Sitophilus* spp.,*Otiorrhyhchus sulcatus, Cosmopolites sordidus, Ceuthorrhynchus assimilis, Hypera postica, Dermestes* spp., *Trogoderma* spp.,*Anthrenus* spp., *Attagenus* spp.,*Lyctus* spp.,*Meligethes aeneus, Ptinus* spp., *Niptus hololeucus, Gibbium psylloides, Tribolium* spp.,*Tenebrio molitor, Agriotes* spp.,*Conoderus* spp.,*Melolontha melolontha, Amphimallon solstitialis, Costelytra zealandica* and *Lissorhoptrus oryzophilus*.

From the order of the Hymenoptera, for example,*Diprion* spp.,*Hoplocampa* spp., *Lasius* spp.,*Monomorium pharaonis* and *Vespa* spp.

From the order of the Diptera, for example,*Aedes* spp., *Anopheles* spp.,*Culex* spp., *Drosophila melanogaster, Musca* spp.,*Fannia* spp.,*Calliphora erythrocephala, Lucilia* spp.,*Chrysomyia* spp.,*Cuterebra* spp.,*Gastrophilus* spp., *Hyppobosca* spp., *Stomoxys* spp.,*Oestrus* spp.,*Hypoderma* spp.,*Tabanus* spp.,*Tannia* spp.,*Bibio hortulanus, Oscinella frit, Phorbia* spp.,*Pegomyia hyoscyami, Ceratitis capitata, Dacus oleae, Tipula paludosa, Hylemyia* spp. and *Liriomyza* spp.

From the order of the Siphonaptera, for example,*Xenopsylla cheopis* and *Ceratophyllus* spp.

From the class of the Arachnida, for example,*Scorpio maurus, Latrodectus mactans, Acarus siro, Argas* spp.,*Ornithodoros* spp.,*Dermanyssus gallinae, Eriophyes ribis, Phyllocoptruta oleivora, Boophilus* spp.,*Rhipicephalus* spp., *Amblyomma* spp., *Hyalomma* spp.,*Ixodes* spp.,*Psoroptes* spp.,*Chorioptes* spp.,*Sarcoptes* spp., *Tarsonemus* spp.,*Bryobia praetiosa, Panonychus* spp.,*Tetranychus* spp; *Hemitarsonemus* spp.,*Brevipalpus* spp.

The phytoparasitic nematodes include, for example, *Pratylenchus* spp.,*Radopholus similis, Ditylenchus dipsaci, Tylenchulus semipenetrans, Heterodera* spp.,*Globodera* spp.,*Meloidogyne* spp.,*Aphelenchoides* spp.,*Longidorus* spp.,*Xiphinema* spp., *Trichodorus* spp.,*Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be employed as such or in their formulations as a mixture with known fungicides, bactericides, acaricides, nematicides or insecticides in order, for example, to increase the activity spectrum or avoid the development of resistance. In many cases synergistic effects are achieved, ie. the efficacy of the mixture is greater than the efficacy of the individual components.

Suitable co-components in mixtures are, for example, the following compounds:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methylbenzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyltetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitrobenzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxymethanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[3,4-dimethoxyphenyl)-3-(4-fluorophenyl)-acryloyl]-morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses,*Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan,*Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos,*Metharhizium anisopliae, metharhizium flavoviride*, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole,*Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2-(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione, 2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxybenzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(-methyl-2-propenyl)-1,2-hydrazinedicarbothioamide,
N-methyl-N'-2-propenyl-1,2-hydrazinedicarbothioamide,
O,O-diethyl-[2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as by a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with novel properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, harvest mites, flies (biting and licking), parasitic fly larvae, lice, hair lice, feather lice and fleas. These parasites include:

From the order of the Anoplurida, for example,*Haematopinus* spp.,*Linognathus* spp.,*Pediculus* spp.,*Phtirus* spp. and *Solenopotes* spp.

From the order of the Mallophagida and the suborders Amblycerina and Ischnocerina, for example,*Trimenopon* spp.,*Menopon* spp.,*Trinoton* spp.,*Bovicola* spp.,*Werneckiella* spp.,*Lepikentron* spp.,*Damalina* spp.,*Trichodectes* spp. and *Felicola* spp.

From the order of the Diptera and the suborders Nematocerina and Brachycerina, for example,*Aedes* spp.,*Anopheles* spp.,*Culex* spp.,*Simulium* spp.,*Eusimulium* spp., *Phlebotomus* spp.,*Lutzomyia* spp.,*Culicoides* spp.,*Chrysops* spp., *Hybomitra* spp., *Atylotus* spp.,*Tabanus* spp.,*Haematopota* spp.,*Philipomyia* spp.,*Braula* spp.,*Musca* spp.,*Hydrotaea* spp.,*Stomoxys* spp.,*Haematobia* spp.,*Morellia* spp.,*Fannia* spp., *Glossina* spp.,*Calliphora* spp.,*Lucilia* spp.,*Chrysomyia* spp.,*Wohlfahrtia* spp., *Sarcophaga* spp.,*Oestrus* spp.,*Hypoderma* spp.,*Gasterophilus* spp.,*Hippobosca* spp.,*Lipoptena* spp. and *Melophagus* spp.

From the order of the Siphonapterida, for example *Pulex* spp.,*Ctenocephalides* spp., *Xenopsylla* spp. and *Ceratophyllus* spp.

From the order of the Heteropterida, for example,*Cimex* spp.,*Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials in the present connection are to be understood as meaning non-living materials, such as, preferably, plastics, adhesives, sizes, paper and card, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic-chemical solvent or solvent mixture and/or an oily or oil-like organic-chemical solvent or solvent mixture of low volatility and/or a polar organic-chemical solvent or solvent mixture and/or water, and if appropriate an emulsifier and/or wetting agent.

Organic-chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic-chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic-chemical solvent or solvent mixture or an aliphatic polar organic-chemical solvent or solvent mixture is replaced. Aliphatic organic-chemical solvents containing hydroxyl and/or ester and/or ether groups, such as, for example, glycol ethers, esters or the like, are preferably used.

Organic-chemical binders which are used in the context of the present invention are the synthetic resins and/or binding drying oils which are known per se, are water-dilutable and/or are soluble or dispersible or emulsifiable in the organic-chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic-chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic-chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268.

The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butylcarbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., in particular fouling by sessile Entomostraka groups, which come under the generic term *Cirripedia* (*cirriped crustaceans*), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S, S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as fentin acetate, metaldehyde, methiocarb, niclosamid, thiodicarb and trimethacarb or conventional antifouling active compounds such as 4,5-dichloro-2-octyl-4-isothiazolin-3-one, diiodomethylparatryl sulphone, 2-(N,N-di-methylthiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985,37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible.

Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl,-isopropyl-L,-methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl,-sodium), flurenol (-butyl), fluridone, fluroxypyr (-butoxypropyl,-meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl,-P-methyl), hexazinone, imazamethabenz (-methyl), imazamethapyr, imazamox, imazapic, imazapyr, imazaquin, imazethapyr, imazosulfuron, iodosulfuron (-methyl,-sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl,-P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example:

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example No. I-1-1

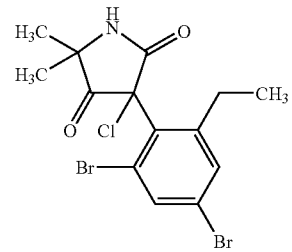

At 0-5° C. and under argon, 0.16 ml of sulphuryl chloride (0.002 mol) in 3 ml of chloroform is added dropwise to 0.78 g of the compound of Example I-1-a-53 from EP-A-825 982 (0.002 mol) in 20 ml of anhydrous chloroform. The reaction mixture is heated under reflux for 4 hours. The mixture is then washed twice with in each case 10 ml of $NaHCO_3$ solution, the filtrate is dried and the solvent is distilled off. The product is purified by column chromatography on silica gel (dichloromethane:ethyl acetate 10:1).

Yield: 0.6 g (71% of theory). M.p. 165° C.

Analogously to Example I-1-1 and in accordance with the general statements for the preparation, the following compounds of the formula (I-1) are obtained

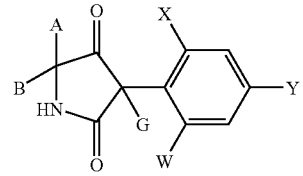

(I-1)

| Ex. No. | W | X | Y | A | B | G | m.p. ° C. |
|---|---|---|---|---|---|---|---|
| I-1-2 | $C_2H_5$ | H | Br | $CH_3$ | $CH_3$ | Cl | 160 |
| I-1-3 | $C_2H_5$ | $C_2H_5$ | Br | $CH_3$ | $CH_3$ | Cl | 164 |
| I-1-4 | $C_2H_5$ | Cl | Cl | $CH_3$ | $CH_3$ | Cl | 120 |
| I-1-5 | $C_2H_5$ | $CH_3$ | Br | i-$C_3H_7$ | $CH_3$ | Cl | oil |
| I-1-6 | $C_2H_5$ | $CH_3$ | Cl | $CH_3$ | $CH_3$ | Cl | 130 |
| I-1-7 | $C_3H_7$ | Br | Br | $CH_3$ | $CH_3$ | Cl | 172 |
| I-1-8 | $C_2H_5$ | Cl | Br | $CH_3$ | $CH_3$ | Cl | 132 |
| I-1-9 | $C_2H_5$ | Br | Cl | $CH_3$ | $CH_3$ | Cl | 145 |
| I-1-10 | $C_2H_5$ | Br | $CH_3$ | $CH_3$ | $CH_3$ | Cl | oil |
| I-1-11 | $C_2H_5$ | Br | $CH_3$ | —$(CH_2)_2$—$CHCH_3$—$(CH_2)_2$— | | Cl | 212 |
| I-1-12 | $C_2H_5$ | Br | Br | —$(CH_2)_2$—$CHCH_3$—$(CH_2)_2$— | | Cl | 209 |
| I-1-13 | $C_2H_5$ | $C_2H_5$ | Cl | —$(CH_2)_2$—$CHCH_3$—$(CH_2)_2$— | | Cl | 210 |
| I-1-14 | $C_2H_5$ | Br | Cl | —$(CH_2)_2$—$CHCH_3$—$(CH_2)_2$— | | Cl | 220 |
| I-1-15 | $C_2H_5$ | $C_2H_5$ | Br | —$(CH_2)_2$—$CHCH_3$—$(CH_2)_2$— | | Cl | 214 |
| I-1-16 | $C_2H_5$ | $CH_3$ | Cl | —$(CH_2)_2$—$CHCH_3$—$(CH_2)_2$— | | Cl | 206 |
| I-1-17 | $C_3H_7$ | Br | Br | —$(CH_2)_2$—$CHCH_3$—$(CH_2)_2$— | | Cl | 217 |
| I-1-18 | $C_2H_5$ | H | Br | —$(CH_2)_2$—$CHCH_3$—$(CH_2)_2$— | | Cl | 182 |
| I-1-19 | $C_2H_5$ | $CH_3$ | Br | —$(CH_2)_2$—$CHCH_3$—$(CH_2)_2$— | | Cl | 225 |
| I-1-20 | $C_2H_5$ | Cl | Cl | —$(CH_2)_2$—$CHCH_3$—$(CH_2)_2$— | | Cl | 230 |
| I-1-21 | $C_2H_5$ | Br | $CH_3$ | —$(CH_2)_5$— | | Cl | 154 |
| I-1-22 | $C_2H_5$ | Br | $CH_3$ | ▷ | $CH_3$ | Cl | foam |
| I-1-23 | $C_2H_5$ | Br | $CH_3$ | $C_2H_5$ | $C_2H_5$ | Cl | 158-164 |
| I-1-24 | $C_2H_5$ | Br | $CH_3$ | $C_3H_7$ | $CH_3$ | Cl | oil |

-continued

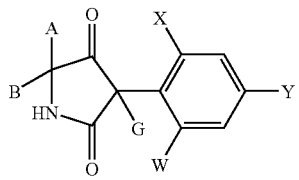

(I-1)

| Ex. No. | W | X | Y | A | B | G | m.p. ° C. |
|---|---|---|---|---|---|---|---|
| I-1-25 | C₂H₅ | C₂H₅ | Br | i-C₃H₇ | CH₃ | Cl | oil |
| I-1-26 | C₂H₅ | C₂H₅ | Br | —(CH₂)₅— | | Cl | 211 |
| I-1-27 | C₂H₅ | C₂H₅ | Br | CH₃ | H | Cl | wax |
| I-1-28 | C₂H₅ | C₂H₅ | Br | C₆H₅—CH₂ | H | Cl | 139 |
| I-1-29 | C₂H₅ | C₂H₅ | Br | i-C₃H₇ | H | Cl | 135 |
| I-1-30 | C₂H₅ | C₂H₅ | Br | i-C₄H₉ | H | Cl | 144 |
| I-1-31 | C₂H₅ | CH₃ | Br | CH₃ | CH₃ | Cl | 91 |
| I-1-32 | C₂H₅ | CH₃ | Br | CH₃ | H | Cl | oil |
| I-1-33 | C₂H₅ | CH₃ | Br | C₆H₅CH₂ | H | Cl | oil |
| I-1-34 | C₂H₅ | CH₃ | Br | i-C₄H₉ | H | Cl | 117 |
| I-1-35 | C₂H₅ | CH₃ | Br | —(CH₂)₅— | | Cl | 188 |
| I-1-36 | C₂H₅ | Br | Br | —(CH₂)₅— | | Cl | oil |
| I-1-37 | C₂H₅ | Br | Br | i-C₃H₇ | H | Cl | oil |
| I-1-38 | C₂H₅ | Cl | Cl | —(CH₂)₅— | | Cl | 181 |
| I-1-39 | C₂H₅ | Cl | Br | —(CH₂)₅— | | Cl | 192 |
| I-1-40 | C₂H₅ | Cl | Br | —(CH₂)₂—CHCH₃—(CH₂)₂— | | Cl | 226 |
| I-1-41 | C₂H₅ | Br | Cl | —(CH₂)₅— | | Cl | 155 |

Example I-2-1

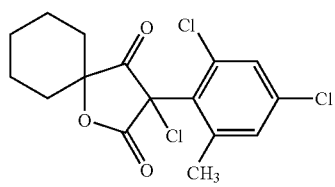

0.982 g (3.0 mmol) according to Ex. No. I-2-a-1 (WO 96/35664) is dissolved in 30 ml of tetrahydrofuran, 0.358 g (3.30 mmol) of tert-butyl hypochlorite is added dropwise and the mixture is stirred at room temperature for 6 h and concentrated using a rotary evaporator. The crude product is purified by column chromatography on silica gel (mobile phase dichloromethane).

Yield: 0.90 g (75% of theory), m.p. 108-110° C.

Analogously to Example I-2-1 and in accordance with the general statements for the preparation, the following compounds of the formula (I-2) are obtained

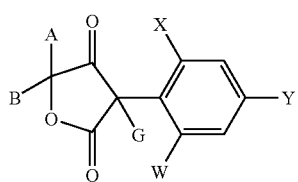

(I-2)

| Ex. No. | W | X | Y | A | B | G | m.p. ° C. |
|---|---|---|---|---|---|---|---|
| I-2-2 | CH₃ | CH₃ | Br | —(CH₂)₅— | | Cl | 123-125 |
| I-2-3 | CH₃ | Br | CH₃ | —(CH₂)₅— | | Cl | 98-100 |

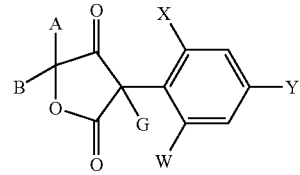

(I-2)

| Ex. No. | W | X | Y | A | B | G | m.p. ° C. |
|---|---|---|---|---|---|---|---|
| I-2-4 | CH₃ | Cl | CH₃ | —(CH₂)₅— | | Cl | 120-122 |
| I-2-5 | C₂H₅ | CH₃ | Br | —(CH₂)₅— | | Cl | *1.25 (t, 3H, CH₂CH₃) 2.40 (s, 3H, ArCH₃) |
| I-2-6 | CH₃ | Br | Br | —(CH₂)₅— | | Cl | 118-120 |
| I-2-7 | CH₃ | CH₃ | Cl | —(CH₂)₅— | | Cl | 95 |
| I-2-8 | CH₃ | Cl | Br | —(CH₂)₅— | | Cl | 88-90 |
| I-2-9 | C₂H₅ | Br | CH₃ | —(CH₂)₅— | | Cl | *1.35 (t, 3H, CH₂CH₃) 2.35 (s, 3H, Ar—CH₃) |

*¹H-NMR (400 MHz, CDCl₃): shifts δ in ppm.

USE EXAMPLES

Example A

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction Example B Pre-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sewn in normal soil. After about 24 hours, the soil is sparyed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction

TABLE C

| | Plant-damaging nematodes Meloidogyne test | |
|---|---|---|
| Active compounds | Concentration of active compound in ppm | Effect in % after 14$^d$ |
| Ex. I-1-3 | 20 | 100 |
| Ex. I-1-1 | 20 | 100 |

Example D

Tetranychus Test (OP-Resistant/Spray Treatment)
Solvents: 78 parts by weight of acetone
    1.6 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of the leaves of beans (*Phaseolus vulgaris*) which are infested by all stages of the greenhouse red spider mite (*Tetranychus urticae*) are sprayed with a preparation of active compound of the desired concentration.

After the desired period of time, the activity in % is determined. 100% means that all spider mites have been killed; 0% means that none of the spider mites have been killed.

| post-emergence | g ai/ha | Sugar beet | Alopecurus | Avena fatua | Echinochloa | Setaria |
|---|---|---|---|---|---|---|
| Ex. I-1-2 | 250 | 0 | 95 | 100 | 100 | 100 |
| Ex. I-1-3 | 250 | 0 | 95 | 100 | 100 | 95 |

| pre-emergence | g ai/ha | Alopecurus | Avena fatua | Echinochloa | Setaria |
|---|---|---|---|---|---|
| Ex. I-1-3 | 250 | 100 | 95 | 100 | 100 |

Example C

Meloidogyne Test
Solvents: 78 parts by weight of acetone
    1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls develop.

After the desired period of time, the nematicidal action is determined in % by the formation of galls. 100% means that no galls have been found; 0% means that the number of galls on the treated plants corresponds to that of the untreated control.

In this test, for example, the following compounds of the Preparation Examples show good activity:

In this test, for example, the following compounds of the Preparation Examples show good activity:

TABLE D

| | Plant-damaging mites Tetranychus test (OP-resistant/spray treatment) | |
|---|---|---|
| Active compound | Concentration of active compound in ppm | Kill rate in % after 4$^d$ |
| Ex. I-1-2 | 100 | 80 |
| Ex. I-1-3 | 100 | 80 |
| Ex. I-1-1 | 100 | 80 |

Example E

In vitro test for the $ED_{50}$ determination in microorganisms

A methanolic solution of the active compound to be tested, admixed with emulsifier PS16 is pipetted into the wells of microtiter plates. After the solvent has evaporated, 200 µl of potato/dextrose medium are added to each well.

Beforehand, a suitable concentration of spores or mycelium of the fungus to be tested was added to the medium.

The resulting concentrations of the active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes 50% inhibition of fungal growth compared to the untreated control ($ED_{50}$) is calculated from the data measured at different concentrations.

TABLE E

In vitro test for the $ED_{50}$ determination in microorganisms

| Active compound | Microorganisms | $ED_{50}$ value |
|---|---|---|
| Ex. I-1-2 | Rhizoctonia solani | 2.04 |
| Ex. I-1-3 | Rhizoctonia solani | 1.37 |
| Ex. I-1-1 | Rhizoctonia solani | 1.66 |

Example F

*Plasmopara* Test (Grapevine)/Protective
Solvents: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corrresponds to that of the control, whereas an efficacy of 100% means that no infection is observed.

TABLE F

Plasmopara test (grapevine)/protective

| Active compound | Application rate of active compound in g/ha | efficacy in % |
|---|---|---|
| Ex. I-1-2 | 750 | 87 |
| Ex. I-1-3 | 750 | 75 |

Example G

Critical Concentration Test/Soil Insects—Treatment of Transgenic Plants
Test insect: *Diabrotica balteata*—larvae in soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultiva YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example H

*Heliothis Virescens* Test—Treatment of Transgenic Plants
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soyabean shoots (*Glycine max*) of the cultiva Roundup Ready (trademark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

What is claimed is:
1. A compound of formula (I)

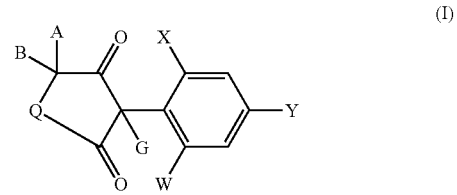

in which
Q represents oxygen or N—H,
W represents methyl, ethyl, or n-propyl,
X represents hydrogen, chlorine, bromine, methyl or ethyl,
Y represents chlorine, bromine, methyl, or ethyl,
with the proviso that at least one of the radicals X or Y represents halogen,
A represents methyl, ethyl, n-propyl, isopropyl, n-butyl, sec-butyl, isobutyl, tert-butyl, trifluoromethyl, benzyl, cyclopropyl, cyclopentyl, or cyclohexyl,
B represents hydrogen, methyl, or ethyl, or
A, B, and the carbon atom to which they are attached represent saturated $C_6$-cycloalkyl that is optionally monosubstituted by methyl,
with the proviso that when Q represents oxygen, A and B together must form an optionally substituted $C_6$-cycloalkyl, and
G represents chlorine.

2. A compound of formula (I) according to claim 1 in which
Q represents NH,
W represents ethyl or n-propyl,
X represents methyl, ethyl, chlorine, or bromine,
Y represents chlorine, bromine, methyl, or ethyl,
with the proviso that at least one of the radicals X or Y represents halogen,
A represents methyl, ethyl, n-propyl, isopropyl, isobutyl, cyclopropyl, or benzyl,
B represents hydrogen, methyl, or ethyl, or
A, B, and the carbon atom to which they are attached represent saturated $C_6$-cycloalkyl that is optionally substituted by methyl, and
G represents chlorine.

3. A compound of formula (I) according to claim 1 in which
Q represents NH,
W represents methyl or ethyl,
X represents hydrogen,
Y represents chlorine or bromine,
A represents methyl,
B represents methyl, or
A, B, and the carbon atom to which they are attached represent saturated $C_6$-cycloalkyl that is optionally monosubstituted by methyl, and
G represents chlorine.

4. A compound of formula (I) according to claim 1 in which
Q represents oxygen,
W represents methyl or ethyl,
X represents methyl, chlorine, or bromine,
Y represents methyl, bromine, or chlorine,
with the proviso that at least one of the radicals X or Y represents halogen,
A, B, and the carbon atom to which they are attached represent saturated Ce-cycloalkyl that is optionally monosubstituted by methyl, and
G represents chlorine.

5. A process for preparing a compound of formula (I) according to claim 1 comprising for compounds of formulas (I-1) to (I-2)

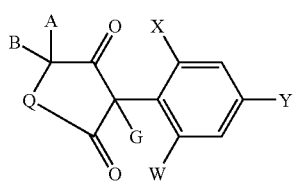

(I-1) to (I-2)

in which
A, B, Q, W, X, and Y are as defined for formula (I) of claim 1, and
G represents halogen, reacting a compound of formulas (II-1) to (II-2)

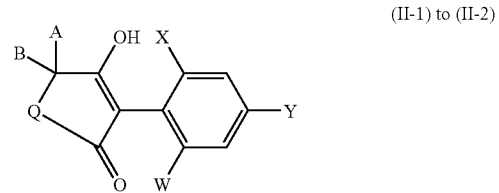

(II-1) to (II-2)

in which A, B, Q, W, X, and Y are as defined for formula (I) of claim 1, with a halogenating agent in the presence of a solvent and, optionally, in the presence of a free-radical initiator.

6. A pesticide or herbicide composition comprising one or more compounds of formula (I) according to claim 1 and one or more extenders and/or surfactants.

7. A method for controlling animal pests comprising allowing an effective amount of one or more compounds of formula (I) according to claim 1 to act on animal pests and/or their habitat.

8. A process for preparing a pesticide or herbicide composition comprising mixing one or more compounds of formula (I) according to claim 1 with one or more extenders and/or surfactants.

9. A method for controlling unwanted vegetation comprising allowing an effective amount of one or more compounds of formula (I)

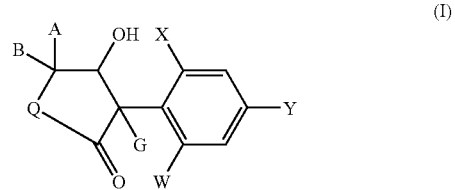

(I)

in which
Q represents oxygen or N—H,
W represents $C_1$-$C_4$-alkyl,
X represents hydrogen, halogen, or $C_1$-$C_4$-alkyl,
Y represents halogen or $C_1$-$C_2$-alkyl,
with the proviso that at least one of the radicals X or Y represents halogen,
A represents $C_1$-$C_8$-alkyl, $C_1$-$C_4$-haloalkyl, $C_1$-$C_4$-alkoxy-$C_1$-$C_2$-alkyl, or benzyl; or represents $C_3$-$C_6$-cycloalkyl that is optionally mono- or disubstituted by $C_1$-$C_4$-alkyl, $C_1$-$C_4$-alkoxy, or halogen,
B represents hydrogen or $C_1$-$C_4$-alkyl, or
A, B, and the carbon atom to which they are attached represent saturated $C_3$-$C_8$-cycloalkyl that is optionally mono- or disubstituted by $C_1$-$C_4$-alkyl or $C_1$-$C_2$-haloalkyl, and
G represents chlorine or bromine, to act on unwanted vegetation and/or its habitat.

* * * * *